United States Patent [19]

Yeakey et al.

[11] Patent Number: 5,116,465

[45] Date of Patent: May 26, 1992

[54] REMOVAL OF WATER, METHANOL AND ACETONE FROM PROPYLENE OXIDE BY EXTRACTIVE DISTILLATION

[75] Inventors: Ernest L. Yeakey; Edward T. Marquis, both of Austin, Tex.

[73] Assignee: Texaco Chemical Company, White Plains, N.Y.

[21] Appl. No.: 786,688

[22] Filed: Nov. 1, 1991

[51] Int. Cl.⁵ .................... B01D 3/40; C07D 301/32
[52] U.S. Cl. ......................... 203/57; 203/14; 203/59; 203/60; 203/64; 549/541
[58] Field of Search .......... 203/59, 57, 58, 60, 203/14, 64, 63, 71, 78, 73, 84; 549/541, 542

[56] References Cited

U.S. PATENT DOCUMENTS

| | | | |
|---|---|---|---|
| 3,265,593 | 8/1966 | Leis et al. | 203/64 |
| 3,715,284 | 2/1973 | Burns et al. | 549/541 |
| 3,838,020 | 9/1974 | Kageyama et al. | 203/64 |
| 4,369,096 | 1/1983 | Seifert et al. | 203/58 |
| 5,006,206 | 4/1991 | Shih et al. | 549/541 |

Primary Examiner—Wilbur Bascomb, Jr.
Attorney, Agent, or Firm—Jack H. Park; Kenneth R. Priem; Carl G. Ries

[57] ABSTRACT

An extractive distillation agent consisting essentially of 2-hydroxyethyl 2-hydroxyethylcarbamate, and is fed to an extractive distillation column used for the distillation of propylene oxide contaminated with water to obtain an overhead distillate fraction consisting of essentially anhydrous propylene oxide, and a heavier bottoms distillation fraction containing substantially all of the 2-hydroxyethyl 2-hydroxyethycarbamate, and water introduced into the disillation column.

4 Claims, 1 Drawing Sheet

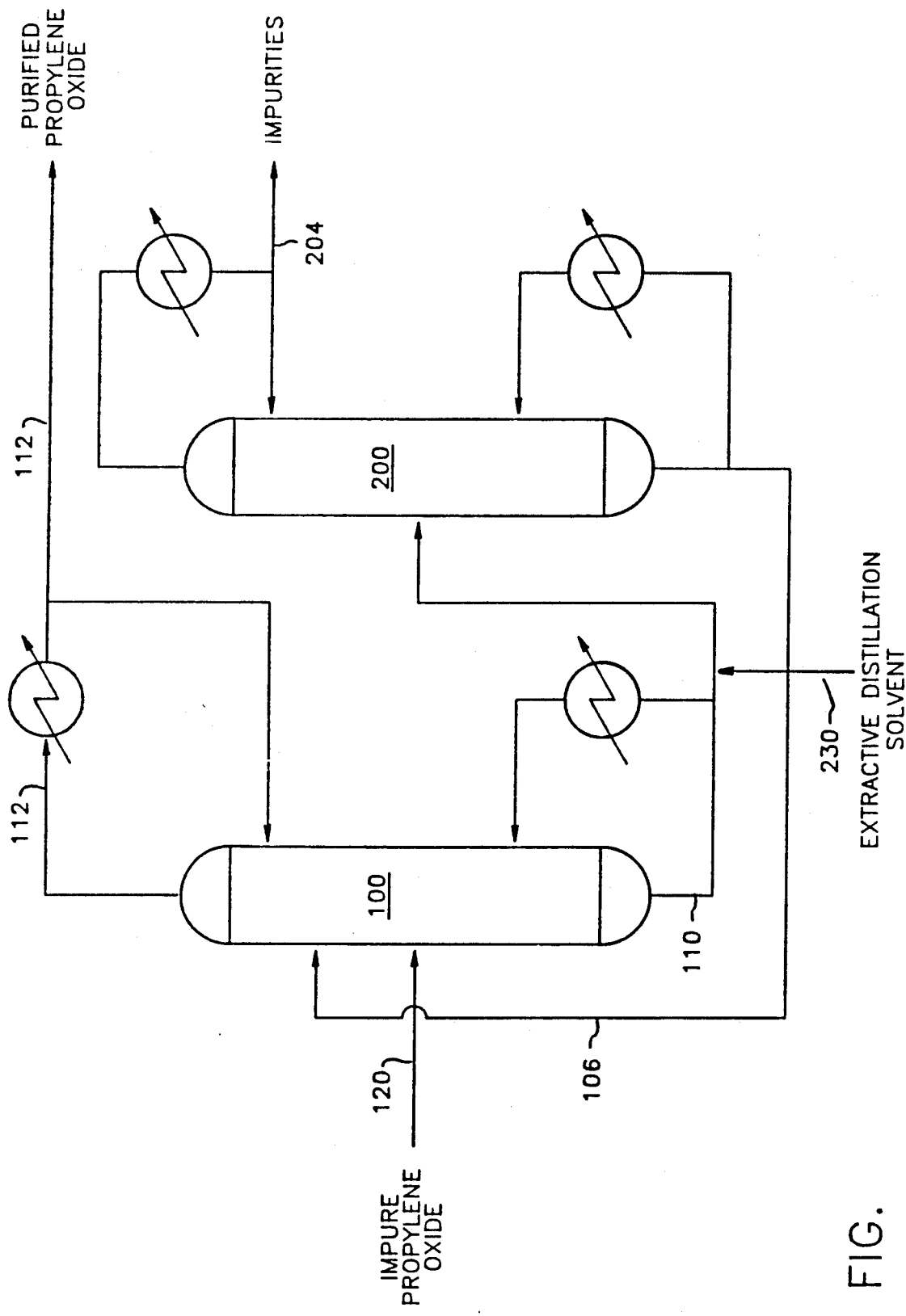

5,116,465

REMOVAL OF WATER, METHANOL AND ACETONE FROM PROPYLENE OXIDE BY EXTRACTIVE DISTILLATION

BACKGROUND OF THE INVENTION

1. Technical Field of the Invention

This invention relates to the purification of propylene oxide. More particularly, this invention relates to a distillation process for removing contaminating quantities of impurities including oxygen-containing impurities such as water, methanol and acetone from an impure propylene oxide feedstock. Still more particularly, this invention relates to a method wherein an impure propylene oxide feedstock contaminated with from about 50 to about 4,000 ppm of methanol, from about 0.01 to about 2 wt. % of water and from about 0.01 to about 2 wt. % of acetone is purified in an extractive distillation column using 2-hydroxyethyl 2-hydroxyethylcarbamate as an extractive distillation agent.

2. Prior Art

It is known to react a hydroperoxide feedstock such as tertiary butyl hydroperoxide with propylene in the presence of an epoxidation catalyst in order to provide a reaction product comprising propylene oxide, an alcohol corresponding to the hydroperoxide feedstock, a solvent, and impurities (see, for example, Kollar U.S. Pat. No. 3,350,422, Kollar U.S. Pat. No. 3,351,635 and Sorgenti U.S. Pat. No. 3,666,777.

It is also known to separate the reaction product by distillation in order to obtain a plurality of fractions including, for example, a propylene recycle fraction, a propylene oxide product fraction, an alcohol fraction, etc.

It is also known that methanol, acetone and water are common contaminants for propylene oxide which are removed only with difficulty.

The propylene oxide that is prepared in this manner is contaminated with water, as is propylene oxide prepared by other processes. Propylene oxide prepared by a peroxidation process of the type exemplified by Kollar U.S. Pat. No. 3,350,422 will also be contaminated with other oxygen-containing impurities such as methanol, acetone, methyl acetate, acetaldehyde, methyl formate, propionaldehyde, etc.

It has heretofore been proposed to purify propylene oxide by extractive distillation and a variety of extractive distillation solvents have been proposed for this purpose. However, there are problems.

In Kageyama et al. U.S. Pat. No. 3,838,020, which is directed to a process for purifying propylene oxide utilizing two extractive distillation columns and two extractive distillation solvent systems (e.g., a first distillation solvent comprising 1,3-butylene glycol, 1,4-butylene glycol, isobutylene glycol, glycerine and mixtures thereof and a second extractive distillation solvent comprising dioxane, butyl acetate, 2-ethylhexanol and mixtures thereof) points out that it is difficult to remove water and other impurities from propylene oxide by extractive distillation with a single solvent and that a single solvent will normally remove either water or organic impurities, but not both.

Among the extractive distillation solvents that have been proposed are materials such as alkanes, alkenes and naphthenes containing 8 to 20 carbon atoms (Schmidt U.S. Pat. No. 3,843,488) aromatic hydrocarbons containing 6 to 12 carbon atoms (Schmidt et al. U.S. Pat. No. 3,909,366), and primary amines (Seifert et al. U.S. Pat. No. 4,369,096).

Robeson et al. U.S. Pat. No. 2,622,060 discloses a process for the purification of propylene oxide contaminated with impurities, including methanol, by subjecting the impure propylene oxide to distillation in the presence of an extractive distillation agent comprising an aqueous solution of an alkali. The inventors report in Example 1 of their patent a method wherein 500 parts by weight of a crude propylene oxide fraction was extractively distilled in accordance with their invention to obtain 325 parts by weight of a product containing about 99.6 wt. % of propylene oxide. Thus, a significant loss of propylene oxide occurred during the process.

Washall U.S. Pat. No. 3,578,568 discloses a process for removing oxygen-containing impurities such as acetone, acetaldehyde and methanol from impure propylene oxide using a glycol such as ethylene glycol or propylene glycol as an extractive distillation agent.

Hoorl and Newman U.S. Pat. No. 3,632,482 is directed to a propylene oxide recovery process by extractive distillation using an alcohol-ketone-hydrocarbon solvent. The invention relates to a method for the purification of crude propylene oxide contained in a mixture produced by the epoxidation of propylene with an organic hydroperoxide and calls for extractive distillation of the crude propylene oxide in a plurality of successive extractive distillation zones with the aid of a solvent mixture consisting essentially of hydrocarbons, alcohols, and/or ketones corresponding to the organic hydroperoxide employed in producing the propylene oxide. In the preferred embodiment of their invention, the extractive distillation agent is a recycle fraction from a three column distillation sequence wherein the bottoms from the third distillation column are flashed to obtain an overhead composed of hydrocarbons, alcohols and/or ketones which is recycled as an extractive distillation agent to the three distillation columns involved in the propylene oxide purification sequence.

Burns et al. U.S. Pat. No. 3,715,284 discloses a process for the purification of impure propylene oxide using acetone or a mixture of acetone with methanol which is introduced into a distillation column either below or together with the impure propylene oxide.

Schmidt U.S. Pat. No. 3,881,996 is directed to a distillation sequence employing at least three and optionally four columns for the purification of crude propylene oxide, one of the columns optionally being an extractive distillation column wherein a hydrocarbon such as octane is used as the extractive distillation agent.

Schmidt U.S. Pat. No. 4,140,588 discloses a process for the purification of propylene oxide contaminated with methanol and acetone using water as an extractive distillation agent, the water being introduced into the distillation column above the point of introduction of the crude propylene oxide feed.

Schmidt states at column 2, lines 50-55 that: "Propylene oxide, however, has a substantial solubility in water and is readily hydrolyzed to propylene glycol (PG) in the presence of large amounts of water"—i.e., in the reboiler section of the tower.

U.S. Pat. No. 4,971,661 discloses the use of an aqueous acetone extraction to remove methanol from propylene oxide.

U.S. Pat. No. 3,578,568 discloses the use of glycols or glycol ethers in an extractive distillation to remove oxygen containing impurities such as acetone, acetaldehyde, and methanol. It is claimed that the concentration of the solvent in the vapor space in the extractive distillation zone of the distillation tower is preferably between 15 and 50 mole percent of the total vapor.

Compared to U.S. Pat. No. 3,578,568, this invention uses considerably lower concentrations of solvent in the extractive distillation zone to remove water and oxygencontaining impurities such as acetone. Since the concentration of the 2-hydroxyethyl 2-hydroxyethylcarbamate is lower, the size and heat requirements of the associated 2-hydroxyethyl 2-hydroxyethylcarbamate regenerator are reduced.

U.S. Pat. No. 4,140,588 discloses the use of water in an extractive distillation to remove methanol and acetone.

U.S. Pat. No. 3,607,669 discloses the use of a $C_8$ to $C_{12}$ hydrocarbon to separate propylene oxide from water.

Shih et al. U.S. Pat. No. 5,000,825 discloses the purification of monoepoxides such as propylene oxide that are contaminated with oxygenated impurities such as water, low molecular weight alcohols, low molecular weight ketones, low molecular weight aldehydes and the like by the extractive distillation of the contaminated monoepoxide using a lower glycol containing 2 to 4 carbon atoms. Examples of lower glycols that are given in the patent include ethylene glycol, 1,2-propane diol, 1,3-propane diol, 1,4-butane diol, 1,2-butane diol, 1,3-butane diol and 2,3-butane diol. It is stated that higher diols or higher glycol ethers do not provide sufficient selectivity for the removal of such impurities and are not included as the extractive distillation solvents suitable for use in the invention.

Mitchell et al. U.S. Pat. No. 2,550,847 is directed to a process for separating purified propylene oxide from a crude propylene oxide product contaminated with acetaldehyde, methyl formate, methanol, etc., by treating the crude mixture with an aqueous basic substance followed by recovery of the purified propylene oxide by any suitable means such as by decantation. Mitchell et al. reported a recovery of a product containing 78 to 82 wt. % of propylene oxide which, they stated, could be increased in purity to about 95 to 99% by fractional distillation.

SUMMARY OF THE INVENTION

In accordance with the present invention, an impure propylene oxide feedstock contaminated with 0.01 to 2 wt. % of water, from about 50 to about 4,000 ppm of methanol and from about 0.01 to about 2 wt. % of acetone is charged to the lower half of an extractive distillation column containing at least about 10 theoretical plates and an extractive distillation agent consisting essentially of 2-hydroxyethyl 2-hydroxyethylcarbamate is charged to the tower at a point at least 4 stages above the impure propylene oxide feed point. Preferably, the extractive distillation tower will contain from about 30 to about 120 theoretical plates and the extractive distillation agent will be charged to the tower at a point of from 7 to 50 theoretical stages above the impure propylene oxide feed point. The extractive distillation agent is introduced into the extractive distillation column in the ratio of said feedstock to said extractive distillation agent of from about 1:1 to about 20:1, and more preferably 2:1 to 10:1, whereby a light distillate fraction is obtained consisting essentially of propylene oxide contaminated with significantly reduced amounts of water, methanol and acetone, such as about 5 to about 600 ppm of water, about 15 to 4,000 ppm of methanol and about 0.1 to about 100 ppm of acetone.

BACKGROUND OF THE PRESENT INVENTION

When propylene is reacted in liquid phase with an organic hydroperoxide such as tertiary butyl hydroperoxide in solution in a solvent such as tertiary butyl alcohol in the presence of a soluble epoxidation catalyst such as a molybdenum epoxidation catalyst, a reaction mixture is formed comprising propylene oxide, an alcohol corresponding to the organic hydroperoxide feedstock and impurities including water and other oxygenated impurities such as methyl formate, acetaldehyde, acetone and methanol.

Propylene oxide is a hygroscopic substance, so that water is removed only with difficulty. It is important to remove as much of the water as possible, however, because the water present in the propylene oxide will tend to react with the propylene oxide to form propylene glycol.

It is also important to reduce the level of other oxygenated contaminants such as methanol and acetone to the lowest reasonably attainable level.

In accordance with conventional practice, an epoxidation reaction product formed by the molybdenum-catalyzed reaction of propylene oxide with tertiary butyl hydroperoxide in solution in tertiary butyl alcohol is separated into the principle components by distillation so as to form distillation fractions including a propylene distillation fraction, a propylene oxide distillation fraction, a tertiary butyl alcohol distillation fraction and a heavy distillation fraction containing the molybdenum catalyst and other products and by-products of the epoxidation reaction. However, the distillation fractions that are thus-obtained are characterized by the inclusion of impurities and, normally, must be further treated if commercially acceptable products are to be obtained. This is especially true for a propylene oxide distillation fraction contaminated with water and oxygenated contaminants including methanol and acetone.

It has been surprisingly discovered in accordance with the present invention that substantially all of the water initially present in a contaminated propylene oxide feedstock can be removed therefrom when the propylene oxide feedstock is extractively distilled in the presence of an extractive distillation agent consisting essentially of 2-hydroxyethyl 2-hydroxyethylcarbamate. Even more surprising is our discovery that substantially all of the acetone and most of the methanol present in the contaminated feedstock can also be removed from the propylene oxide when using 2-hydroxyethyl 2-hydroxyethylcarbamate as the extractive distillation agent.

BRIEF DESCRIPTION OF THE DRAWING

The drawing is a schematic flow sheet with conventional parts omitted showing the general recovery sequence that is used in accordance with the present invention in purifying propylene oxide.

In the drawing, for convenience, the present invention is illustrated in connection with a process wherein the propylene oxide is prepared by the epoxidation of propylene with tertiary butyl hydroperoxide in solution in tertiary butyl alcohol to provide a reaction product comprising propylene oxide and additional tertiary butyl alcohol.

DESCRIPTION OF THE PREFERRED EMBODIMENT

Turning now to the drawing, there is shown a schematic flow sheet illustrating a preferred method of practicing the process of the present invention. In the drawing, conventional parts such as valves, pumps, temperature sensors, pressure sensors, heaters, coolers, flow control regulation apparatus, etc., have been omitted.

In accordance with a preferred embodiment of the present invention, propylene oxide is separated in a preliminary distillation zone (not shown) from other components of an epoxidation reaction mixture in order to provide an impure propylene oxide fraction contaminated with oxygen-containing impurities such as acetone, methanol, water, etc.

The impure propylene oxide feedstock that is thus obtained in the preliminary distillation zone is then purified in a propylene oxide purification distillation zone, which in accordance with the preferred embodiment of the present invention, comprises two distillation columns, each of which is equipped with an appropriate reflux condensing means and an appropriate reboiler heating means.

In accordance with the present invention, an impure propylene oxide fraction contaminated with from about 50 to about 4,000 ppm of methanol, from about 0.01 to about 2 wt. % of acetone and about 0.01 to about 2 wt. % of water and other oxygen-containing impurities is charged by way of a line 120 leading to a distillation column 100 which, in accordance with the present invention, will preferably be a column containing at least about 10 theoretical plates and more preferably, from about 30 to about 100 theoretical plates. The column 100 is suitably operated under distillation conditions including a pressure of about 10 to 40 psia, a reflux ratio of from about 2:1 to about 10:1, a reboiler temperature within the range of about 100° to about 250° C. (e.g., 210° C.) and a top temperature of about 20° to about 80° C. (e.g., about 20° C.).

The impure propylene oxide is preferably charged to the distillation column 100 in the lower half thereof. An extractive distillation agent consisting essentially of 2-hydroxyethyl 2-hydroxyethylcarbamate is charged to the upper half of the distillation column 100 by an extractive distillation charge line 106.

Essentially anhydrous purified propylene oxide containing about 100 ppm or less of water is removed from the column 100 as a light distillation fraction 112, the purified propylene oxide in the line 112 containing significantly reduced amounts of methanol and acetone, such as about 15 to 900 ppm of methanol and about 0.1 to 100 ppm of acetone. A heavier fraction 110 is withdrawn from the distillation column 100 which contains substantially all of the extractive distillation agent charged by the line 106 and also substantially all of the water, acetone and other oxygen-containing impurities introduced into the column 100 with the impure propylene oxide 120.

The heavier distillation fraction 110 from the column 100 comprising water, methanol, acetone, tertiary butyl alcohol and other impurities and extractive distillation agent is charged to a second distillation column 200 wherein light impurities such as methanol, acetone, water, etc., are separated overhead as a distillation fraction 204 that is discharged from the system for any suitable use, such as for use as a steam boiler feedstock or for recovery.

A heavier distillation fraction 106 is discharged from the distillation column 200 comprising 2-hydroxyethyl 2-hydroxyethylcarbamate which is recycled to distillation column 100 by line 106.

The compound 2-hydroxyethyl 2-hydroxyethylcarbamate has the formula:

2-Hydroxyethyl 2-hydroxyethylcarbamate is a high boiling liquid isolated as a bottoms product from the reaction of monoethanolamine and ethylene carbonate, prepared as described in U.S. Pat. No. 3,595,814, Example I.

If industrial grades of 2-hydroxyethyl 2-hydroxyethylcarbamate were introduced directly into the column 100, a substantial amount of undesired contaminating water would also be introduced. In accordance with the present invention, the fresh 2-hydroxyethyl 2-hydroxyethylcarbamate either as the original charge, or as make-up solvent, is introduced into the system by a branch line 230 leading to the charge line 110 for the second distillation column 200 so that any water introduced into the system with the fresh 2-hydroxyethyl 2-hydroxyethylcarbamate will be separated therefrom in the column 200 and withdrawn from the column 200 through the line 204.

EXAMPLES

The invention will be further illustrated by the following specific examples which are given by way of illustration and not as limitations on the scope of this invention. Where parts are mentioned, they are parts by weight.

Comparative distillation runs were made without the use of an extractive distillation solvent and with 2-hydroxyethyl 2-hydroxyethylcarbamate as the solvent. The results are tabulated below. The runs were conducted in a 25 actual plate pilot plant distillation column at an operating pressure of 14–18 psia.

| Component | No Solvent: | | | MeOH/ Acetone ppm |
|---|---|---|---|---|
| | Feed wt % | Water Overhead ppm | Bottoms wt % | |
| PO | 99.00 | — | — | |
| Acetone | 0.70 | — | — | |
| Methanol | 0.20 | — | — | |
| Water | 0.17 | 784 | 2.1 | 1052/5 |

| Component | 2-Hydroxyethyl 2-Hydroxyethylcarbamate Extraction Solvent: | | | | MeOH/ Acetone ppm |
|---|---|---|---|---|---|
| | Feed wt % | Solvent wt % | Water Overhead ppm | Bottoms wt % | |
| PO | 99.0 | — | — | — | |
| Acetone | 0.70 | — | — | — | |
| Methanol | 0.20 | — | — | — | |
| Water | 0.17 | 0.236 | — | — | |
| 2-Hydroxyethyl 2-hydroxyethyl-carbamate | — | 99.602 | 340 | 0.461 | 28/2.2 |

Solvent:Feed ratio 0.33 (lb/lb)

Water and oxygen-containing impurities such as acetone and methanol are difficult to remove from propylene oxide by standard distillation. The use of extractive distillation columns with 2-hydroxyethyl 2-hydroxyethylcarbamate as the solvent improves the separation of these impurities from propylene oxide.

Having thus described our invention, what is claimed is:

1. An extractive distillation process for the distillation of an impure propylene oxide feedstock in a distillation column to remove oxygenated contaminants, including water, acetone and some of the methanol from the impure propylene oxide feedstock which comprises the steps of:

introducing said impure propylene oxide feedstock into the lower half of a distillation column, introducing an extractive distillation agent consisting essentially of 2-hydroxyethyl 2-hydroxyethylcarbamate above the impure propylene oxide feed point, said extractive distillation agent being introduced into said distillation column in the ratio of said feedstock to said extractive distillation agent of from about 1:1 to about 20:1, withdrawing an overhead distillate fraction from said distillation column consisting essentially of essentially anhydrous propylene oxide contaminated with reduced quantities of acetone and methanol, withdrawing a bottoms distillation fraction from said distillation column containing substantially all of the 2-hydroxyethyl 2-hydroxyethylcarbamate, and substantially all of the water, methanol and acetone introduced into said distillation column.

2. An extractive distillation process as in claim 1 wherein the said impure propylene oxide feedstock comprises propylene oxide contaminated with from about 0.1 to about 2 wt. % of water, from about 50 to about 4000 ppm of methanol and from about 0.1 to about 2 wt. % of acetone.

3. An extractive distillation process for the distillation of an impure propylene oxide feedstock in a distillation column which comprises the steps of:

charging said impure propylene oxide feedstock to the lower half of a distillation column containing at least 25 theoretical plates, said impure propylene oxide feedstock comprising propylene oxide contaminated with from about 0.1 to 2 wt. % of water, from about 50 to about 4000 ppm of methanol and from about 0.1 to about 2 wt. % of acetone, introducing an extractive distillation agent consisting essentially of 2-hydroxyethyl 2-hydroxyethylcarbamate, at a point at least 4 theoretical plates above the impure propylene oxide feed point, said extractive distillation agent being introduced into said distillation column in the ratio of said feedstock to said extractive distillation agent of from about 1:1 to about 20:1, withdrawing an overhead distillate fraction from said distillation column consisting essentially of essentially anhydrous propylene oxide contaminated with reduced quantities of acetone and methanol, and withdrawing a bottoms distillation fraction from said distillation column containing substantially all of the 2-hydroxyethyl 2-hydroxyethylcarbamate, and substantially all of the water, methanol and acetone introduced into said distillation column.

4. An extractive distillation process for the distillation of impure propylene oxide in a distillation column, which comprises the steps of:

introducing an impure propylene oxide feedstock into the lower half of a distillation column containing at least 25 theoretical plates, said impure propylene oxide feedstock comprising propylene oxide contaminated with from about 0.1 to about 2 wt. % of water, from about 50 to about 4000 ppm of methanol and from about 0.1 to about 2 wt. % of acetone, introducing an extractive distillation agent consisting essentially of 2-hydroxyethyl 2-hydroxyethylcarbamate, at a point at least 4 theoretical plates above the impure propylene oxide feed point, said extractive distillation agent being introduced into said distillation column in the ratio of said feedstock to said extractive distillation agent of from about 1:1 to about 20:1, fractionating said impure propylene oxide feedstock in said distillation column under distillation conditions including a pressure of about 10 to about 40 psia, a reflux ratio of from about 1:1 to about 5:1, a reboiler temperature within the range of about 100° to about 250° C. and a top temperature of about 20° to about 80° C., withdrawing an overhead purified propylene oxide distillate fraction from said distillation column consisting essentially of essentially anhydrous propylene oxide, said purified propylene oxide distillate fraction being contaminated with a significantly reduced amount of acetone, and withdrawing a bottoms distillation fraction from said distillation column containing substantially all of the 2-hydroxyethyl 2-hydroxyethylcarbamate, and substantially all of the water, methanol and acetone introduced into said distillation column.

* * * * *